United States Patent [19]

Repinec, Jr. et al.

[11] Patent Number: 5,284,603
[45] Date of Patent: Feb. 8, 1994

[54] GELLED DETERGENT COMPOSITION HAVING IMPROVED SKIN SENSITIVITY

[75] Inventors: Stephen T. Repinec, Jr., Flemington; Gilbert S. Gomes, Somerset, both of N.J.; Rita Frilli, Rocourt, Belgium

[73] Assignee: Colgate Palmolive Co., New York, N.Y.

[21] Appl. No.: 59,865

[22] Filed: May 10, 1993

Related U.S. Application Data

[63] Continuation-in-part of Ser. No. 893,138, Jun. 3, 1992, abandoned.

[51] Int. Cl.$^5$ .................. C11D 1/831; C11D 1/84
[52] U.S. Cl. .................. 252/546; 252/549; 252/550; 252/554; 252/555; 252/558; 252/559; 252/173; 252/174.21; 252/DIG. 1; 252/DIG. 14
[58] Field of Search ............ 252/549, 550, 554, 555, 252/558, 559, 546, 173, 174.21, DIG. 1, DIG. 14

[56] References Cited

U.S. PATENT DOCUMENTS

| | | |
|---|---|---|
| 3,962,418 | 6/1976 | Birkofer .................. 252/547 |
| 4,420,410 | 12/1983 | Hüttinger .................. 252/550 |
| 4,595,526 | 6/1986 | Lai .................. 252/500 |
| 4,784,800 | 11/1988 | Leng et al. .................. 252/557 |
| 4,844,821 | 7/1989 | Mermelstein et al. .................. 252/550 |
| 4,898,690 | 2/1990 | Bitter et al. .................. 252/554 |
| 4,992,107 | 2/1991 | Itoku et al. .................. 252/558 |
| 4,992,213 | 2/1991 | Mallett et al. .................. 252/174.21 |

FOREIGN PATENT DOCUMENTS 50-076106  6/1975  Japan .

Primary Examiner—Paul Lieberman
Assistant Examiner—Bradley A. Swope
Attorney, Agent, or Firm—Richard E. Nanfeldt; Robert C. Sullivan; Murray Grill

[57] ABSTRACT

A high foaming, nonionic surfactant based, light duty, liquid detergent with desirable cleansing properties and mildness to the human skin comprising three essential surfactants: a water soluble nonionic surfactant as the major active ingredient, in an amount in excess of 50% by weight of the total surfactant content; a supplemental amount of a water soluble, foaming, anionic surfactant excluding the ethoxylated alkyl ether sulfates; and a lesser amount of a water soluble, foaming zwitterionic betaine surfactant.

9 Claims, No Drawings

GELLED DETERGENT COMPOSITION HAVING IMPROVED SKIN SENSITIVITY

RELATED APPLICATION

This application is a continuation in part application of U.S. Ser. No. 07/893,138 filed Jun. 3, 1992 now abandoned.

BACKGROUND OF THE INVENTION

The present invention relates to novel gelled light duty liquid detergent compositions with high foaming properties, containing a nonionic surfactant as the major active ingredient supplemented with lesser amounts of a specific group of anionic surfactants and even a Zwitterionic betaine surfactant in an aqueous medium, wherein the weight ratio of the anionic surfactant to the Zwitterionic betaine surfactant is about 1.2:1 to 1:1.2.

Nonionic surfactants are in general chemically inert and stable toward pH change and are therefore well suited for mixing and formulation with other materials. The superior performance of nonionic surfactants on the removal of oily soil is well recognized. Nonionic surfactants are also known to be mild to human skin. However, as a class, nonionic surfactants are known to be low or moderate foamers. Consequently, for detergents which require copious and stable foam, the application of nonionic surfactants is limited. There have been substantial interest and efforts to develop a high foaming gelled detergent with nonionic surfactants as the major ingredient. Yet, little has been achieved.

The prior art is replete with light duty liquid detergent compositions containing nonionic surfactants in combination with anionic and/or betaine surfactants, wherein the nonionic detergent is not the major active surfactant, as shown in U.S. Pat. No. 3,658,985, wherein an anionic based shampoo contains a minor amount of a fatty acid alkanolamide. U.S. Pat. No. 3,769,398 discloses a betaine-based shampoo containing minor amounts of nonionic surfactants. This patent states that the low foaming properties of nonionic detergents renders its use in shampoo compositions non-preferred. U.S. Pat. No. 4,329,335 also discloses a shampoo containing a betaine surfactant as the major ingredient and minor amounts of a nonionic surfactant and of a fatty acid mono- or di ethanolamide. U.S. Pat. No. 4,259,204 discloses a shampoo comprising 0.8-20% by weight of an anionic phosphoric acid ester and one additional surfactant which may be either anionic, amphoteric, or nonionic. U.S. Pat. No. 4,329,334 discloses an anionic-amphoteric based shampoo containing a major amount of anionic surfactant and lesser amounts of a betaine and nonionic surfactants.

U.S. Pat. No. 3,935,129 discloses a liquid cleaning composition based on the alkali metal silicate content and containing five basic ingredients, namely, urea, glycerin, triethanolamine, an anionic detergent and a nonionic detergent. The silicate content determines the amount of anionic and/or nonionic detergent in the liquid cleaning composition. However, the foaming property of these detergent compositions is not discussed therein.

U.S. Pat. No. 4,129,515 discloses a heavy duty liquid detergent for laundering fabrics comprising a mixture of substantially equal amounts of anionic and nonionic surfactants, alkanolamines and magnesium salts, and, optionally, zwitterionic surfactants as suds modifiers.

U.S. Pat. No. 4,224,195 discloses an aqueous detergent composition for laundering socks or stockings comprising a specific group of nonionic detergents, namely, an ethylene oxide of a secondary alcohol, a specific group of anionic detergents, namely, a sulfuric ester salt of an ethylene oxide adduct of a secondary alcohol, and an amphoteric surfactant which may be a betaine, wherein either the anionic or nonionic surfactant may be the major ingredient. The specific class of anionics utilized in this patent is the very same group of anionic detergents expressly excluded in present invention in order to eliminate the alkanol ethoxylate sulfation process and the potential dioxane toxicity problem. Furthermore, this patent finds heavily foaming detergents undesirable for the purpose of washing socks.

The prior art also discloses detergent compositions containing all nonionic surfactants as shown in U.S. Pat. Nos. 4,154,706 and 4,329,336 wherein the shampoo compositions contain a plurality of particular nonionic surfactants in order to effect desirable foaming and deteresive properties despite the fact that nonionic surfactants are usually deficient in such properties.

U.S. Pat. No. 4,013,787 discloses a piperazine based polymer in conditioning and shampoo compositions which may contain all nonionic surfactant or all anionic surfactant.

U.S. Pat. No. 4,450,091 discloses high viscosity shampoo compositions containing a blend of an amphoteric betaine surfactant, a polyoxybutylenepolyoxyethylene nonionic detergent, an anionic surfactant, a fatty acid alkanolamide and a polyoxyalkylene glycol fatty ester. But, none of the exemplified compositions contains an active ingredient mixture wherein the nonionic detergent is present in major proportion, probably due to the low foaming properties of the polyoxybutylene polyoxyethylene nonionic detergent.

U.S. Pat. No. 4,595,526 describes a composition comprising a nonionic surfactant, a betaine surfactant, an anionic surfacant and a $C_{12}$–$C_{14}$ fatty acid monethanolamide foam stabilizer.

However, none of the above-cited patents discloses a gelled high foaming, nonionic based, liquid detergent composition containing a nonionic surfactant as a major active ingredient and minor amounts of a supplementary high foaming anionic sulfate or sulfonate surfactant excluding ethoxylated alcohol ether sulfates, a supplementary foaming zwitterionic surfactant selected from betaine type surfactants as the three essential ingredients, wherein the nonionic surfactant ingredient constitutes the major constituent and the composition does not contain any amine oxide, abrasives, polymeric or clay thickeners, fatty acid alkanolamides, alkali metal carbonates such as calcium carbonate, clays, silicas or more than 3 wt. % of a fatty acid or a metal salt of the fatty acid.

SUMMARY OF THE INVENTION

It has now been found that a high foaming liquid detergent can be formulated with a nonionic surfactant as the major active ingredient which has desirable cleaning properties, mildness to the human skin and avoids the dioxane toxicity problem associated with the sulfation process of manufacturing anionic ethoxylated alcohol ether sulfates.

Accordingly, one object of the invention is to provide novel gelled, high foaming, nonionic based, light duty liquid detergent compositions containing a nonionic ionic surfactant as the major constituent.

Another object of this invention is to provide novel, gelled, nonionic based, liquid detergent compositions containing a major amount of nonionic surfactant supplemented with lesser amounts of an anionic surfactant and a zwitterionic betaine surfactant, wherein the composition does not contain, amine oxide, fatty acid alkanolamide, polymeric or clay thickeners, alkali metal carbonate, clays, silica, and abrasive or more than 3 wt. % of a fatty acid or a metal salt of the fatty acid.

Still another object of this invention is to provide a novel, gelled, nonionic based, liquid detergent with desirable high foaming and cleaning properties which is mild to the human skin.

A further object of this invention is to provide a novel, nonionic based liquid detergent containing an anionic surfactant excluding the ethoxylated alkyl ether sulfates which eliminates the alkanol ethoxylate sulfation process and the potential dioxane toxicity problem.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein the novel, gelled, high foaming, nonionic based, light duty liquid detergent of this invention comprises three essential surfactants a water soluble, nonionic surfactant as the major active ingredient; of a foaming anionic surfactant selected from the group consisting of water soluble organic sulfates and organic sulfonates, excluding the ethoxylated alkyl ether sulfates; and of a zwitterionic surfactant selected from the class of betaines, wherein the three surfactants are dissolved in an aqueous vehicle, and the composition does not contain any amine oxide, fatty acid alkanolamide, clay, abrasive, silica, polymeric or clay thickeners, alkali metal carbonate, or more than 3 wt. % of a fatty acid or its salt. The instant gelled compositions have a melting temperature transition of at least 32°0 C., a G' value of at least 4,000 N/m$^2$ and a G" value of at least 1000 N/m$^2$ at 25° C.

More specifically, the present invention relates to a gelled high foaming, nonionic based, liquid detergent containing an nonionic surfactant selected from the group consisting of water soluble primary aliphatic alcohol ethoxylates secondary aliphatic alcohol ethoxylates, alkyl phenol ethoxylates and alcohol ethylene oxide propylene oxide condensates; an anionic surfactant selected from the group consisting of water soluble salts of $C_8$–$C_{18}$ alkyl sulfates, $C_8$–$C_{16}$ benzene sulfonates, $C_{10}$–$C_{20}$ paraffin sulfonates, alpha $C_{10}$–$C_{24}$ olefin sulfontaes, $C_8$–$C_{18}$ alkyl sulfoacetates, $C_8$–$C_{18}$ alkyl sulfosuccinate esters, $C_8$–$C_{18}$ acyl isethionates and $C_8$–$C_{18}$ acyl taurates; and a water soluble zwitterionic betaine surfactant, wherein the three surfactants are dissolved in an aqueous vehicle.

This particular combination of three ingredients in the proportions, by weight, as specified hereinafter, the nonionic surfactant, anionic surfactant and the betaine surfactant wherein a ratio of the anionic surfactant to the betaine surfacant is about 1.2:1 to about 1:1.2, is critical to the formation of the gel state high foaming and desirable cleansing properties of present liquid detergent and the retention of the mildness to the skin property. The total amount of surfactants may constitute about 26%–42%, preferably about 28%–40%, most preferably 30%–38%, by weight of the liquid composition.

DETAILED DESCRIPTION OF THE INVENTION

The gelled, high foaming, nonionic based, light duty liquid detergent compositions of the instant invention comprise approximately by weight: 16 to 24% of a water soluble nonionic surfactant; 14 to 25% of a water-soluble anionic detergent; 5 to 9% of a water soluble betaine and the balance being water, wherein the compositions do not contain any anionic alkyl ether polyethenoxy sulfate detergent, amine oxide, alkali metal carbonate, polymeric or clay thickeners, abrasive, clay, silica or more than 3 wt. % of a fatty acid or a metal salt of the fatty acid and the ratio of the anionic detergent to the betaine is about 1.2: 1 to 1:1.2 and the gelled composition has a melting temperature of at least 32° C., a G' value at 25° C. of at least about 4,000 N/m$^2$ and a G" value at 25° C. of at least about 1,000 N/m$^2$.

The nonionic surfactant which constitutes the major ingredient in present liquid detergent is present in amounts of about 16%–24%, preferably 17%–23%, most preferably 18%–21%, by weight of the composition and provides superior performance in the removal of oily soil and mildness to human skin.

The water soluble nonionic surfactants utilized in this invention are commercially well known and include the primary aliphatic alcohol ethoxylates, secondary aliphatic alcohol ethoxylates, alkylphenol ethoxylates and ethylene-oxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic detergent class includes the condensation products of a higher alcohol (e.g., an alkanol containing about 8 to 18 carbon atoms) condensed with about 5 to 30 moles of ethylene oxide, for example, laurylmyristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

The more preferred group of the foregoing nonionic surfactants are the Neodol ethoxylates (Shell Co.), which are higher aliphatic, primary alcohol containing about 9-15 carbon atoms, condensed with 6.5 to 15 moles of ethylene oxide such as a $C_9$-$C_{11}$ primary alcohol condensed with 8 moles of ethylene oxide (Neodol 91-8), $C_{12-13}$ alkanol condensed with 6.5 moles ethylene oxide (Neoldol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Such ethoxamers have an HLB (hydrophobic lipophilic balance) value of about 8-15 and give good o/w emulsification, whereas ethoxamers with HLB values below 8 contain less than 5 ethyleneoxy groups and tend to be poor emulsifiers and poor detergents. Specially preferred Neodols are: Neodol 1-9 ($C_{11}$alkanol condensed with 9 moles of ethylene oxide), Neodol 25-9($C_{12-15}$ alcohol condensed with 9 moles of ethylene oxide and Neodol 25-12($C_{12-15}$ alkanol condensed with 12 moles of ethylene oxide).

Additional satisfactory water soluble alcohol ethylene oxide condensates are the condensation products of a secondary aliphatic alcohol containing 8 to 18 carbon atoms condensed with 5 to 30 moles of ethylene oxide. Examples of commercially available nonionic detergents of the foregoing type are $C_{11}$-$C_{15}$ secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from about 8 to 18 carbon atom alkyl group with about 5 to 30 moles of ethylene oxide. Specific examples of alkyl phenol ethoxylates include nonyl phenol condensed with about 9.5 moles of EO per mole of nonyl phenol, dinonyl phenol condensed with about 12 moles of EO per mole of phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

Also among the satisfactory nonionic detergents are the water-soluble condensation products of a $C_8$-$C_{20}$ alkanol with a heteric mixture of ethylene oxide and propylene oxide wherein the weight ratio of ethylene oxide to propylene oxide is from 2.5:1 to 4:1, preferably 2.8:1-3.3:1, with the total of the ethylene oxide and propylene oxide (including the terminal ethanol or propanol group) being from 60-85%, preferably 70-80%, by weight. Such detergents are commercially available from BASF-Wyandotte and a particularly preferred detergent is a $C_{10}$-$C_{16}$ alkanol condensate with ethylene oxide and propylene oxide, the weight ratio of ethylene oxide to propylene oxide being 3:1 and the total alkoxy content being about 75% by weight.

Condensates of 2 to 30 moles of ethylene oxide with sorbitan mono- and tri-$C_{10}$-$C_{20}$ alkanoic acid esters having a HLB of 8 to 15 also may be employed as the nonionic detergent ingredient in the described compositions. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

Other suitable water-soluble nonionic detergents which are less preferred are marketed under the trade name "Pluronics." The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L 62 and L 64. Another suitable nonionic surfacants Lauropol 02 sold by Witco Chemical or Synperionic 91 sold by ICI Europe and Lialet 111 sold by Enichem, Dehydol sold by Henkel and Genapol sold by Hoechst.

The anionic surfactant, which is an essential ingredient of present liquid detergent composition, constitutes about 5% to 10%, preferably 6%-9%, by weight thereof and provides good foaming properties. However, preferably reduced amounts are utilized in order to enhance the mildness of the skin property desired in the inventive compositions. In addition, the particular group of anionic surfactants utilized excludes the $C_8$-$C_{18}$ alkyl polyethenoxy ether sulfate surfactants in order to avoid the dioxane toxicity associated with the process of sulfation of ethoxylated alcohols. Thus, the ethoxylated alcohol ether sulfates are expressly excluded from the specific group of anionic surfactants utilized.

The anionic surfactants which may be used in the nonionic based liquid detergent of this invention are water soluble such as triethanolamine and include the sodium, potassium, ammonium and ethanolammonium salts of $C_8$-$C_{18}$ alkyl sulfates such as lauryl sulfate, myristyl sulfate and the like; linear $C_8$-$C_{16}$ alkyl benzene sulfonates; $C_{10}$-$C_{20}$ paraffin sulfonates; alpha olefin sulfonates containing about 10-24 carbon atoms; $C_8$-$C_{18}$ alkyl sulfoacetates; $C_8$-$C_{18}$ alkyl sulfosuccinate esters; $C_8$-$C_{18}$ acyl isethionates; and $C_8C$-$_{18}$ acyl taurates. Preferred anionic surfactants are the water soluble $C_{12}$-$C_{16}$ alkyl sulfates, the $C_{10}$-$C_{15}$ alkylbenzene sulfonates, the $C_{13}$-$C_{17}$ paraffin sulfonates and the alpha $C_{12}$-$C_{18}$ olefin sulfonates.

The water-soluble zwitterionic surfactant, which is also an essential ingredient of present liquid detergent composition, constitutes about 5-9%, preferably 6%-8%, by weight and provides good foaming properties and mildness to the present nonionic based liquid detergent. The zwitterionic surfactant is a water soluble betaine having the general formula:

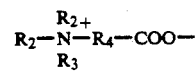

wherein $R_1$ is an alkyl group having 10 to about 20 carbon atoms, preferably 12 to 16 carbon atoms, or the amido radical:

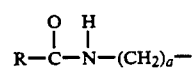

wherein R is an alkyl group having about 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethylammonia) acetate, coco dimethyl betaine or 2-(N-coco N, N-dimethylammonio) acetate, myristyl dimethyl betaine, palmityl dimethyl betaine, lauryl diemthyl betaine, cetyl dimethyl betaine, stearyl dimethyl betaine N lauryl-N, N-dimethyl-N-carboxyl methyl ammonium betaine, etc. The amidobetaines similarly include cocoamidoethylbetaine, cocoamidopropyl betaine and the like. A preferred betaine is coco ($C_8$–$C_{18}$) amidopropyl dimethyl betaine. Two preferred betaine surfactants are Rewoteric AMB 13 Golmschmidt Betaine L7 and Henkel Velvetex BK-35.

The weight ratio of the anionic surfactant to the betaine surfactant is about 1.2:1 to about 1:1.2, more preferably about 1.1:1 to about 1:1.1 and most preferably about 1.05 to about 1:1.05.

All of the aforesaid three ingredients in this gelled light duty liquid detergent are water soluble or water dispersible and remain so during storage.

This particular combination of anionic surfactant and betaine surfactant in nearly equal or equal amounts of anionic surfactant and betaine surfactant, provides a detergent system which coacts with the nonionic surfactant to product a gelled detergent composition with desirable foaming, foam stability, detersive properties and mildness to human skin. Surprisingly, the resultant gelled liquid detergent exhibits the same or better foam performance, both as to initial foam volume and stability of foam in the presence of soils, and cleaning efficacy as an anionic based light duty liquid detergent (LDLD). Inorganic salts such as sodium chloride and sodium citrate can be optionally added at concentrations of 0.01 to 1.0 wt. % to modify the cloud point of the nonionic surfactant and thereby control the haze of the resultant gel. Various other ingredients are added such as urea at a concentration of about 10.0 to 20.0 wt. %. Other ingredients which have been added to the compositions at concentrations of about 0.1 to 4.0 wt. percent are perfumes, chelating agents, fragrances sodium formate, sodium bisulfite, EDTA, and proteins such as Lexeine protein.

In addition to the previously mentioned essential and optional constituents of the light duty liquid detergent, one may also employ normal and conventional adjuvants, provided they do not adversely affect the properties of the gel. Thus, there may be used various coloring agents and perfumes; ultraviolet light absorbers such as the Uvinuls, which are products of GAF Corporation; sequestering agents such as ethylene diamine tetraacetates; magnesium sulfate heptahydrate; pearlescing agents and opacifiers; pH modifiers; etc. The proportion of such adjuvant materials, in total will normally not exceed 15% of weight of the detergent composition, and the percentages of most of such individual components will be a maximum of 5% by weight and preferably less than about 2% by weight. Sodium bisulfite can be used as a color stabilizer at a concentration of about 0.01 to 0.2 wt. %

The present nonionic based light duty liquid detergents such as dishwashing liquids are readily made by simple mixing methods from readily available components which, on storage, do not adversely affect the entire composition. However, it is preferred to form an aqueous solution of the nonionic surfactant, To the aqueous solution of the nonionic surfactant is added with agitation the anionic surfactant and the betaine to and then adding with agitation the formula amount of water to form the gelled detergent composition. The use of mild heating (up to 100° C.) assists in mixing of the surfactants. The viscosities and strength of the gels are adjustable by changing the total percentage of active ingredients. The integrity of the gel and the gel viscosity and the detergent itself remain stable on storage for lengthy periods of time, without color changes or settling out of any insoluble materials. The pH of this formation is substantially neutral to skin, e.g., about 4.5 to 8 and preferably about 5.0 to 5.5.

These products have unexpectedly desirable properties. For example, the foam quality and detersive property is equal to or better than standard light duty liquid detergents while using a nonionic surfactant as the primary surfactant and less amounts of an anionic surfactant, thereby achieving a mild, non-irritating liquid gel.

The gelled detergent composition of the instant invention have a G' value as measured on a CarriMed Rheometer of at least about 4,000 N/m$^2$, more preferably 6,000 N/m$^2$ and most preferably at least about 6,000 N/m$^2$ and a G" value as measured on a Carri Med Rheometer of at least about 1,000 N/m$^2$, more preferably at least about 1,100 N/m$^2$ and most preferably at least about 1,150 N/m$^2$. The gelled detergent composition of the invention have a melting temperature of at least about 32°0 C. and most preferably at least about 34° C.

The following examples which are made by the previously described simple mixing procedure are merely illustrative of the invention and are not to be construed as limiting thereof.

EXAMPLE 1

The following formulas were prepared to the previously defined process.

|  | A | B | C | D | E | F | G |
|---|---|---|---|---|---|---|---|
| Ammonia Lauryl Sulfate | 7 | 7 | 7 | 7 | 7 | 7 | 7 |
| Cocoamido propyl betaine | 7 | 7 | 7 | 7 | 7 | 7 | 7 |
| Neodol 1-9 | 20 |  |  |  |  |  |  |
| Noedol 25-7 |  | 20 |  |  |  |  | 19 |
| Neodol 25-9 |  |  | 20 |  | 20 | 20 |  |
| Neodol 25-12 |  |  |  | 20 |  |  |  |
| Urea |  |  |  |  |  | 15 |  |
| Sodium lauryl sulfate | 0 |  |  |  | 7 |  |  |
| Water | Bal | Bal | Bal | Bal | Bal | Bal | Bal |
| G' at 25° C. |  |  | 7200 |  |  |  | 4500 |
| G" at 25° C. |  |  | 1200 |  |  |  | 1600 |
| Melting Temperature °C. | 35 | 20 | 42 | 60 | 50 | 60 | 33 |
| Shell Foam Tset (ml) |  |  |  |  |  |  | 124 |

Formula G has a Shell Foam value of 124 ml as compared to a value of 100 ml for a commercial Palmolive Hand Dish and at 108 ml for Palmolive Skin Sensitive.

What is claimed is:

1. A high foaming, gelled, light duty, liquid detergent composition comprising approximately, by weight, (a) 16% to 24% of a water soluble nonionic surfactant selected from the group consisting of $C_8-C_{18}$ alkanol condensates with 5 to 30 moles of ethylene oxide, condensates of $C_8-C_{18}$ alkylphenol with 5 to 30 moles of ethylene oxide, condensates of $C_8-C_{20}$ alkanol with a heteric mixture of ethylene oxide and propylene oxides having a weight ratio of ethylene oxide to propylene oxide from 2.5:1 to 4:1 and a total alkylene oxide content of 60% of 85% by weight and condensates of 2 to 30 moles of ethylene oxide with sorbitan mono and tri-$C_{10}-C_{20}$ alkanoic acid esters having an HLB of 8 to 15;

(b) 5% to 9% of a water-soluble or dispersible anionic detergent selected from the group consisting of $C_8-C_{18}$ alkyl sulfates, $C_8-C_{16}$ alkylbenzene sulfonates, $C_{10}-C_{20}$ paraffin sulfonates, $C_{10}-C_{24}$ alpha olefin sulfonates and $C_8-C_{18}$ alkyl sulfosuccinate esters, $C_8-C_{18}$ acyl isethionates and $C_8-C_{18}$ acyl taurates;

(c) 5% to 9% of a water-soluble betaine; and (d) balance being water in which said nonionic surfactant, said anionic detergent and said betaine are gelled in said water, wherein the ratio of B to C is about 1.2:1 to about 1:1.2 and said gelled detergent composition having a melting temperature of at least 32° C. a G; value at 25° C. of at least about 4,000 $N/m^2$ and a G" value at 25° C. of at least about 1,000 $N/m^2$ and said composition does not contain any anionic alkyl ether polyethenoxy sulfate detergent, amine oxide, fatty acid alkanolamide, clay, abrasive, silica, polymeric thickeners, alkali metal carbonate, or more than 3 wt. % of a fatty acid or its salt.

2. A liquid detergent composition according to claim 1 which includes, in addition, 1% to 15% by weight of a solubilizing agent selected from the group consisting of $C_2-C_3$ mono- and di-hydroxy alkanols, water soluble salts of $C_1-C_3$ substituted benzene sulfonate hydrotropes and mixtures thereof.

3. A liquid detergent composition according to claim 2 wherein ethanol is present in the amount of 5% by weight or less.

4. A liquid detergent composition according to claim 2 wherein said nonionic surfactant is said condensate of a primary $C_8-C_{18}$ alkanol with 5-30 moles of ethylene oxide.

5. A liquid detergent composition according to claim 4 wherein said anionic detergent is selected from the group consisting of $C_{12}-C_{16}$ alkyl sulfates, $C_{10}-C_{15}$ alkylbenzene sulfonates, $C_{13}-C_{17}$ paraffin sulfonates and $C_{12}-C_{18}$ alpha olefin sulfonates.

6. A liquid detergent composition according to claim 1 wherein said nonionic surfactant is present in an amount of 16% to 22% by weight, said anionic detergent is present in an amount of 2% to 9% by weight and said betaine is present in an amount of 2% to 9% by weight.

7. A liquid detergent composition according to claim 6 wherein said anionic detergent is a $C_{12}-C_{16}$ alkyl sulfate.

8. A liquid detergent composition according to claim 1 further including a preservative.

9. A liquid detergent composition according to claim 1 further including a color stabilizer.

* * * * *

UNITED STATES PATENT AND TRADEMARK OFFICE
CERTIFICATE OF CORRECTION

PATENT NO. : 5,284,603
DATED : February 8, 1994
INVENTOR(S) : Stephen T. Repinec, Jr; et al It is certified that error appears in the above-indentified patent and that said Letters Patent is hereby corrected as shown below:

On the title page, item [75] Inventors; delete "Frilli" and insert --Erilli--.

Signed and Sealed this

Fourth Day of October, 1994

*Attest:*

BRUCE LEHMAN

*Attesting Officer*  *Commissioner of Patents and Trademarks*